United States Patent [19]

Masurekar et al.

[11] 4,052,263

[45] Oct. 4, 1977

[54] PRODUCTION OF CHOLESTEROL ESTERASE USING *NOCARDIA CHOLESTEROLICUM*

[75] Inventors: Prakash S. Masurekar, Webster; Charles T. Goodhue, Rochester, both of N.Y.

[73] Assignee: Eastman Kodak Company, Rochester, N.Y.

[21] Appl. No.: 639,690

[22] Filed: Dec. 11, 1975

[51] Int. Cl.$^2$ .................. C12D 13/00; C07G 7/02; C12B 1/20

[52] U.S. Cl. ................................. 195/66 R; 195/62; 195/65; 195/114

[58] Field of Search ................ 195/62, 65, 66 R, 114, 195/96

[56] References Cited

U.S. PATENT DOCUMENTS

| | | | |
|---|---|---|---|
| 3,776,816 | 12/1973 | Terada et al. ................. | 195/66 R |
| 3,884,764 | 5/1975 | Goodhue et al. ............. | 195/62 X |
| 3,909,359 | 9/1975 | Goodhue et al. ............. | 195/65 |

FOREIGN PATENT DOCUMENTS

| | | | |
|---|---|---|---|
| 2,246,695 | 3/1973 | Germany ...................... | 195/66 R |
| 733,259 | 4/1973 | South Africa ................ | 195/66 R |
| 1,385,319 | 2/1975 | United Kingdom ........... | 195/62 |

OTHER PUBLICATIONS

Lee, "Degradation Mechanism of Cholesterol and its Derivatives by Microorganisms III," Chemical Abstracts, vol. 77, No. 23, p. 58, Abs. No. 147941f (1972).
Voets et al., "Microbial Degradation of Cholesterol," Chemical Abstracts, vol. 81, No. 1, p. 96, Abs. No. 1140e (1974).
Reese et al., "Surfactants as Stimulants of Enzyme Production by Microorganisms," Applied Microbiology, vol. 17, No. 2 (1969), pp. 242-245.
Research Disclosure, (Oct. 1974), "Method for the Preparation of Cholesterol Oxidase," pp. 46-50.
Sih et al., "An Efficient Synthesis of Estrone and 19--Norsteroids from Cholesterol," Journal of American Chemical Society, vol. 87, No. 12 (1965), pp. 2765-2766.
Korzenousky et al., "Manometric Assay and Properties of Pancreatic Esterase," Biochem. Journal, vol. 76 (1960), pp. 238-245.

*Primary Examiner*—Raymond N. Jones
*Assistant Examiner*—Thomas G. Wiseman
*Attorney, Agent, or Firm*—George W. Neuner

[57] ABSTRACT

An improved fermentation method comprises growing *Nocardia cholesterolicum* in a medium comprising a carbon source, such as glycerol, yeast extract, a nonionic surfactant, an auxiliary carbon source which is also an inducer of cholesterol oxidase, and trace salts. Yields of cholesterol oxidase up to about 900 U. (international units) per liter have been obtained using the improved method of the present invention in contrast with the yields of 1-3 U. per liter obtained in the prior art. Proper selection of environmental conditions also enables the coproduction of cholesterol esterase.

4 Claims, No Drawings

PRODUCTION OF CHOLESTEROL ESTERASE USING *NOCARDIA CHOLESTEROLICUM*

FIELD OF THE INVENTION

The present invention relates to an improved method for the cultivation of *Nocardia cholesterolicum* and more particularly to an improved method for producing cholesterol oxidase. The improved fermentation method also producs cholesterol esterase.

BACKGROUND OF THE INVENTION

Microorganisms capable of metabolizing cholesterol are potential sources of enzymes useful in an enzymatic assay of cholestrol in complex mixtures such as blood serum, etc. This is particularly so if the microorganisms can use cholesterol as a sole carbon source, for in this assay process cholesterol must be degraded by oxidative enzymes.

Stadtman, T. C., *Methods in Enzymology*, Vol. 1; Colowick, S. P., and Kaplan, N. O., Eds. *Academic Press*, N.Y., 1955, p. 678; and Stadtman, T. C., Cherkes, A., and Anfinsen, J., *Biol. Chem.*, 206, 510 (1954), reported the preliminary purification of an enzyme from *Nocardia cholesterolicum*, an organism originally isolated by Schatz et al. (Schatz, A., Savard, K., and Pintner, I. J., *J. Bacteriol.*, 58, 117-125 (1949). Stadtman's enzyme, "cholesterol dehydroenase", was purified sufficiently for use in a cholesterol assay based on the measurement of the increase in absorbance at 250 nm. owing to the formation of cholest-4-en-3-one. Since, as we have now determined, the direct acceptor of cholesterol electrons in this oxidation is oxygen, the enzyme should properly be called cholesterol oxidase according to current convention.

The bacterial strains described by Stadtman when cultured as described in the aforementioned references produce very low enzyme levels which are not practical for commercial operations. These levels are so low that commercial production of purified enzyme is a very remote possibility.

Goodhue et al., in U.S. Pat. No. 3,909,359 issued September 30, 1975, describe an improved method for the production of the Stadtman cholesterol oxidase, which method comprises the steps of:

a. growing the bacterium Nocardia cholsterolicum species NRRL 5767 or NRRL 5768 in a medium in which cholesterol or a suitable derivative thereof serves as an auxiliary source of carbon and b. isolating from said medium cell-free extract containing the active enzyme.

The method described by Goodhue et al is greatly improved over the original synthesis described by Stadtman and can be said to render the process commercially practical.

German OLS 2,246,695 published Mar. 29, 1973, describes a method for isolating a cholesterol oxidase enzyme produced by a culture of Nocardia microoorganism identified as NRRL 5635 and NRRL 5636. According to the method described therein, the harvested cells are treated with a nonionic surfactant and stirred at room temperature to release a large proportion of the enzyme from the cells into the supernatant, thereby eliminating the need for involved cell extraction and isolation techniques. From the data reported, we have calculated the extraction yields enzyme activity on the order of about 40 to 160 U/liter.

Reese, E. T., and Maquire, A., in "Surfactants as Stimulants of Enzyme Production by Microorganisms", *Applied Microbiology*, February, 1969, pp. 242-245, describe the observation that the addition of sorbitan polyoxyethylene monoleate (Tween 80 from Atlas Chemical Co., Wilmington, Delaware) and other nonionic surfactants to fungal cultures which normally produce extracellular enzymes results in a marked increase in enzyme yield.

British Patent 1,385,319 describes the production of cholesterol oxidase from Nocardia species NRRL 5635 and NRRL 5636. The fermentation is conducted in a growth medium containing 20 g./liter of yeast extract. During the fermentation, cholesterol is slowly added to the medium, preferably in the form of a dispersion containing a nonionic surfactant. Cholesterol is added in quantities totaling up to 1.2 g./liter of medium during this addition. The total concentration of nonionic surfactant added in this manner is minute.

Republic of South Africa Patent 73/3259 describes the production of cholesterol oxidase using *Proactinomyces erythropolis NBC* 9158, ATC 17895, ATCC 4277 and *Nocardia formica* ATCC 14811. The fermentation is conducted in a peptone-containing mineral salt medium and, when the logarithmic growth phase is reached, cholesterol in the form of an aqueous suspension is slowly added to the medium in proportion to the growth of the microorganism such that the cholesterol added totals 1 to 20 g./liter of medium. A small amount of cholesterol (0.05% in Example 2) may be added to the medium initially. Increase in the yield of cholesterol oxidase activity is obtained by adding yeast extract to the cholesterol suspension as an emulsifying agent in an amount of 0.02 to 1% by weight of the cholesterol suspension. It can be seen that only a very small amount of yeast extract is added to the medium in this manner. No surfactant is used during the fermentation.

SUMMARY OF THE INVENTION

The present invention provides an improved method for the cultivation of *Nocardia cholesterolicum* which substantially increases the production of cholesterol oxidase over prior-art methods. Growing *Nocardia cholesterolicum* in an improved fermentation medium also yields the enzyeme cholesterol esterase.

The improved fermentation method is accomplished by growing the Nocardia bacterium in a growth medium having a enzyme inducer which may also be an auxiliary carbon source. The growth medium also has from about 1.0 to about 5.0 g./liter of a nonionic surfactant which is nontoxic to the bacterium and at least about 10 g./liter of yeast extract. The above ingredients in the growth medium apparently have a synergistic effect on the production of cholesterol oxidase, giving yields of about 900 U./liter and simultaneously producing the enzymes cholesterol esterase.

DETAILED DESCRIPTION OF THE INVENTION

A microbial cell has the genetic information to synthesize virtually thousands of enzymes. However, enzyme production is tightly controlled to avoid the waste of energy and the intermediates. Therefore, to develop a fermentation, existing control mechanisms in the microbial cells need to be modified so that the desired enzyme or metabolite is overproduced. There are two ways to alter the regulation of the biochemical pathways, namely, (1) environmental and (2) genetic.

The production of cholesterol oxidase is greatly increased by the procedure of this invention by providing appropriate environmental conditions. In addition to producing cholesterol oxidase in high yields, by properly selecting environmental conditions, cholesterol esterase is also produced.

According to the present invention, the production of intracellular cholesterol oxidase is substantially increased by growing *Nocardia cholesterolicum* in a medium comprising yeast extract, a nonionic surfactant and an inducer for cholesterol oxidase, in addition to a carbon source and trace metal salts. Proper selection of the inducer and other environmental conditions also enables the coproduction of cholesterol esterase in usable quantities.

Two *Nocardia choleserolicum* cultures which yield cholesterol oxidase and cholesterol esterase are characterized as the "rough" and "smooth" strains and are called NRRL 5767 and NRRL 5768 respectively based on their deposit with the Agricultural Collection Investigations Fermentation Laboratory, Peoria, Illinois.

Complete details of the organisms are as follows:

Description of *Nocardia cholesterolicum*

I. Cellular morphology
   A. Smooth strain. Gram positive weakly acid-fast, coryneform, no well-developed mycelia, but rudimentary branching observed. Coccoid forms appear in older cultures.
   B. Rough strain. Same as above.
II. Colonial morphology
   A. Nutrient agar (5 days, 30° C).
      1. Smooth strain. Circular, convex, watery, entire, smooth, glistening, pink-white. No soluble pigment.
      2. Rough strain. Circular, convex, entire, smooth to rough, pink-white. No soluble pigment.
   B. Yeast glucose agar (5 days, 30° C.).
      1. Smooth strain. Cream- to tan-colored, watery, smooth, round, elevated.
      2. Rough strain. Dry, cream- to tan-colored, round, elevated.
   C. Casein agar (5 days, 30° C.).
      1. Sooth strain. Cream- to tan-colored, watery, round, smooth, elevated.
      2. Rough colony. Tan to pink, dry, elevated.
   D. Gelatin agar.
      1. Smooth strain. Circular, convex, entire, smooth, watery, cream-colored.
      2. Rough strain. Circular, convex, entire, dry, cream-colored.
III. Growth in liquid culture (nutrient broth, 5 days, 30° C.)
   A. Smooth strain. Off-white to tan flock-forming precipitate, no pellicle.
   B. Rough strain. Off-white to tan flock-forming precipitate, no pellicle.
IV. Physiology (smooth and rough strains identical)

| | |
|---|---|
| aeration | aerobic |
| gelatin hydrolysis | − |
| casein hydrolysis | − |
| starch hydrolysis | − |
| oxidase | − |
| catalase | + |
| urease | − |
| indole | − |
| methyl red | − |
| phenylalanine deamination | − |
| litmus milk | alkaline |
| Use of compounds as sole carbon source | |
| citrate | + |
| lactate | + |
| malate | + |
| succinate | + |
| fructose | + |
| glucose | + |
| sucrose | + |
| maltose | + |
| glycerol | + |
| sorbitol | + |
| trehalose | + |
| raffinose | − |
| dulcitol | − |
| lactose | − |
| mannitol | + |
| starch | − |
| arabinose | − |

According to the method described by Goodhue et al, which produced intracellular cholesterol oxidase, the use of a conventional primary carbon source such as glycerol, in combination with a secondary or auxiliary carbon source such as cholesterol, cholest-4-en-3-one or cholesteryl linoleate, all of which act as cholesterol oxidase inducers, increases the yield of cholesterol oxidase enzyme to levels about 100 times higher than those produced when a cholesterol oxidase inducer is not used or when cholesterol is used as the sole carbon source as described in the prior art.

Thus, according to Goodhue et al, improved yields were obtained when the bacterium was grown in a conventional nutrient medium of the type well-known in the art which generally comprises a nitrogen source such as ammonium sulfate, a potassium and a phosphorus source such as potassium phosphate, trace metal ions, and a mixture of a primary carbon source such as glycerol and a cholesterol oxidase inducer selected from the group consisting of cholesterol, cholest-4-en-3-one, cholesteryl linoleate, and mixtures thereof. The pH value of the medium is maintained between about 5.0 and 8.0, preferably between about 6.5 and 7.5, at a temperature of from about 25° to about 35° C., preferably about 30° C., for a period of from about 18 to about 40 hours, preferably from about 20 to about 24 hours.

The quantities of nitrogen, potassium phosphorus and trace metal ions used in the culture are those conventionally used in processes of this type and are well-known to those skilled in the art. Specifically, those described in the aforementioned references provide useful levels of these constituents.

Among the primary carbon sources which were found useful by Goodhue et al and which are similarly useful herein are glycerol, glucose and acetic acid. Conventional concentrations of primary carbon source are used. These generally range from about 5 g./liter to about 50 g./liter. The concentration of the cholesterol oxidase inducer utilized generally ranges from about 1.0 g./liter to about 10.0 g./liter. A preferred range of inducer is from about 2 g./liter to about 5 g./liter.

According to the improved process described herein, cholesterol oxidase is prepared substantially as described by Goodhue et al except that the growth medium further includes yeast extract and a nonionic surfactant. Inclusion of such materials in the fermentation medium unexpectedly results in a substantial increase in the production of intracellular choleserol oxidase.

It has also been discovered that the process described by Goodhue et al produces cholesterol esterase in addition to the cholesterol oxidase. Proper selection of the growth environment of the Nocardia culture will vary the ratio of oxidase to esterase in the fermentation product.

The inclusion of yeast extract is essential to obtain the high yield of cholesterol oxidase in the improved fermentation process of this invention. The addition of increasing amounts of yeast extract improves the yield of cholesterol oxidase until it reaches a maximum, after which point the continued addition of yeast extract represses the yield of cholesterol oxidase, as will be determined by the examples which follow. The yield of cholesterol oxidase has been increased as much as 5000 percent over the prior art by incorporating optimum quantities of yeast extract into the growth medium. Generally, yeast extract is used in a concentration of at least about 10 g./liter; however, a concentration of from about 10 g./liter to about 30 g./liter is preferred. Optimum results have been achieved using yeast extract in the particularly preferred amount of about 20 g./liter. It should be noted, however, that the quantity of yeast extract which produces optimum results may vary somewhat depending upon the source of the yeast extract.

The production of cholesterol oxidase is strongly affected by the addition of nonionic surfactant to the growth medium. Up to the threefold increases in the enzyme yield were obtained by incorporating small amounts of nonionic surfactant in the growth medium. Nonionic surfactants are well-known in the art and no further definition thereof is required herein. Typical examples of such materials include polyethylene glycol, polyvinyl alcohols, polyethers, polyesters and polyhalides.

Of critical importance to the successful practice of the invention are the criteria that:
1. neither the particular nonionic surfactant used nor its decomposition product is toxic to the microorganism in the concentrations required to increase the yield of enzyme and
2. the amount of surfactant used does not inhibit enzyme production.

The toxicity of the decomposition products of the surfactant can be theorized as described briefly hereinafter; however, the only positive test for such a criterion is evaluation in the growth medium and observation of the effects of by-products produced therein.

Nonionic surfactants include a broad range of materials and any such material which meets the two criteria described hereinabove are useful in the successful practice of the invention.

According to a preferred embodiment wherein cholesterol oxidase is prepared as described hereinabove, the nonionic surfactant has a hydrophilic moiety comprising 20 units of polyoxyethylene and a lipophilic moiety comprising a fatty acid chain having 16 carbon atoms. For the practice of the present invention, nonionic surfactants equivalent to the preferred surfactant described above include nonionic surfactants having a polyoxythylene or polyglycidol hydrophilic moiety and lipophilic moiety comprising at least 9 carbon atoms. Particularly useful nonionic surfactants are those in which the lipophilic moiety comprises a fatty acid chain of at least 10 carbon atoms.

Optimum results are achieved when the fatty acid chain contains at least 16 carbon atoms and the hydrophilic moiety comprises about 20 polyoxyethylene units.

Examples of specific surfactants which are useful in the practice of the instant invention and their structure include:

| HLB | Surfactant | Hydrophile | No. of Units | Lipophile | No. of Units |
|---|---|---|---|---|---|
| 16.7 | S-1 | sorbitan polyoxyethylene | 1 20 | lauric acid | 1 |
| 13.3 | S-2 | sorbitan polyoxyethylene | 1 4 | lauric acid | 1 |
| 15.6 | S-3 | sorbitan polyoxyethylene | 1 20 | palmitic acid | 1 |
| 14.9 | S-4 | sorbitan polyoxyethylene | 1 20 | stearic acid | 1 |
| 6.9 | S-5 | sorbitan polyoxyethylene | 1 4 | stearic acid | 1 |
| 10.5 | S-6 | sorbitan polyoxyethylene | 1 20 | stearic acid | 3 |
| 15.0 | S-7 | sorbitan polyoxyethylene | 1 20 | oleic acid | 1 |
| 10.0 | S-8 | sorbitan polyoxyethylene | 1 5 | oleic acid | 1 |
| 17.1 | S-9 | polyoxyethylene | 10 | nonylphenyl | 1 |
| 15.0 | S-10 | polyoxyethylene | 15 | nonylphenyl | 1 |
| 13.3 | S-11 | polyoxyethylene | 30 | nonylphenyl | 1 |
| 13.3 | S-12 | polyglycidol | 6 | nonylphenyl | 1 |
| 13.5 | S-13 | polyglycidol | 10 | nonylphenyl | 1 |

The concentration of nonionic surfactant used in any particular growth medium will vary considerably depending upon the composition of the medium, the sensitivity of the medium to the particular surfactant and the particular surfactant used. Generally, however, surfactant concentrations of up to about 5.0 g./liter of medium have been found useful in at least certain fermentation media with certain surfactant compositions. At levels above 5.0 g./liter, the surfactant generally tends to inhibit the production of cholesterol oxidase. It is generally preferred, as demonstrated by the exemplary results set forth below, to utilize surfactant concentrations of from about 1.0 to about 3.0 g./liter of medium.

In the production of cholesterol oxidase using a nutrient growth medium containing a nonionic surfactant in accordance with the teachings of this invention, foaming may be encountered. In order to control the foaming, especially when producing large batches, the use of a foam-control agent is advisable. One such foam-control agent found useful in the practice of this invention is polyglycol P-2000, available from Dow Chemical, Midland, Mich. Other foam-control agents can also be used, the main criterion for selection and use being the lack of inhibition of enzyme synthesis at a concentration level which will control the foam.

The growth medium includes a primary carbon source such as, for example, glycerol, glucose, corn syrup, or the like, and an inducer of cholesterol oxidase which may also be a secondary carbon source. Besides the cholesterol, cholest-4-en-3-one and cholesteryl linoleate which were taught as inducers by Goodhue et al, supra, other sterols and cholesterol esters are useful as inducers of cholesterol oxidase. Other preferred inducers include, for example, 3-$\beta$-hydroxy sterols such as $\beta$-sitosterol and 5-$\alpha$-cholestan-3-$\beta$-ol, and other cholesterol esters such as cholesteryl oleate, cholesteryl linolenate, cholesteryl formate and cholesteryl propionate.

The fermentation process described herein is desirably run at a temperature of from about 18° C. to about 35° C. Temperatures below 30° C. are preferred, with temperatures in the range of from 20° C. to about 30° C. being most preferred.

We have further discovered, as noted hereinabove, that *Nocardia cholesterolicum* also produces a cholesterol esterase. This enzyme is induced by cholesterol, cholesterol esters, and certain sterols such as those described above and in the examples. In general, the sterols are better inducers of the esterase. There is a good correlation between the production of cholesterol oxidase and cholesterol esterase from growing *NOcardia cholesterolicum*. However, the ratio of esterase to oxidase varies depending on the inducer.

In the following examples, which are presented to demonstrate better the successful practice of the invention, the following definitions apply:

1. Culture

*Nocardia cholesterolicum* was obtained from Dr. Theresa Stadtman (N.I.H., Bethesda, Md.). A rough colony variant (NRRL 5767) was used unless otherwise stated.

2. Nutrient media

The compositions of media used in the examples are as follows:

| (A) | Glycerol medium | |
|---|---|---|
| | | per liter |
| | ammonium sulfate | 2.0 g. |
| | potassium phosphate (dibasic anhydrous) | 2.0 g. |
| | salt solution "C" | 5.0 ml |
| | glycerol | 5.0 g. |
| | tryptone | 0.1 g. |
| | distilled water | to 1 liter |
| | salt solution "C" | per liter of 0.1N HCl |
| | $MgSO_4 . 7H_2O$ | 25.0 g. |
| | $CaCl_2 . 2H_2O$ | 0.1 g. |
| | $FeSO_4 . 7H_2O$ | 2.8 g. |
| | $MnSO_4 . H_2O$ | 1.7 g. |
| | $ZnSO_4 . 7H_2O$ | 0.06 g. |
| | NaCl | 0.6 g. |
| (B) | Inoculum medium | |
| | | per liter |
| | glucose | 10.0 g. |
| | yeast extract* | 10.0 g. |
| | potassium phosphate (dibasic anhydrous) | 1.0 g. |
| | salt solution A-1 | 2.0 ml. |
| | salt solution A-2 | 2.0 ml. |
| | agar | 20.0 g. |
| | adjust pH to 7.0 and make up to 1 liter with distilled water | |
| | salt solution A-1: | |
| | | per liter |
| | $MgSO_4 . 7H_2O$ | 100.0 g. |
| | $FeSO_4 . 7H_2O$ | 10.0 g. |
| | $MnSO_4 . H_2O$ | 1.0 g. |
| | $NaMoO_4 . 2H_2O$ | 0.5 g. |
| | make up to 1 liter in 0.1N HCl | |
| | salt solution A-2: | |
| | | per liter |
| | $CaCl_2 . 2H_2O$ | 10.0 g. |
| | distilled water | to 1 liter |
| (C) | Modified glycerol medium | |
| | | per liter |
| | ammonium sulfate | 2.0 g. |
| | potassium phosphate (dibasic, anhydrous) | 2.0 g. |
| | salt solution "C" | 5.0 ml. |
| | glycerol | 5.0 g. |
| | surfactant S-3 | 3.0 g. |

-continued

| | |
|---|---|
| yeast extract* | 20.0 g. |
| cholesterol | 1.0 g. |
| distilled water | to 1 liter |

*The yeast extract used is commercially available as Bacto yeast extract from Difco Laboratories, Detroit, Michigan.

3. Maintenance of the Culture

The cultures were maintained on the slants of glycerol medium containing cholesterol and were transferred every second day. In addition, the cultures were also kept frozen in liquid nitrogen.

4. Preparation of inoculum (small-scale use)

An inoculum medium slant was inoculated with *Nocardia cholesterolicum* (rough) from a 2-day-old glycerol medium slant and was incubated at 30° C. for 48 hr. The culture from this slant was scraped off with a wire loop and was resuspended in 25 ml. of sterile distilled water by vigorous shaking. The turbidity of this suspension was generally between 1.8–2.2 O.D. units at 660 nm. Sixty ml. of this suspension were used as inoculum per liter of the growth medium.

5. Preparation of inoculum for large-scale fermentation

*Nocardia cholesterolicum* (rough) grown for 48 hr. on ioculum medium slants was used to inoculate 7.5 liters of sterilized modified glycerol medium in a 14-liter fermenter (Chemapec, Mannedorf, Switzerland). Eight slants were used for this purpose. The medium was aerated at 0.5 vvm. and agitated with flat 3-blade turbine impellers at 1300 rpm. The temperature was maintained at 30° C. After 18 hr. of incubation, the contents of the fermenter were aseptically transferred to a 150-liter fermenter.

6. Fermentation

A. Small-scale

The fermentations were carried out in 250-ml. Erlenmeyer flasks. The volume of medium used in Erlenmeyer flasks was 25 ml. The medium in the flasks was inoculated as described above and was incubated at 30° C. The shaker speed was adjusted to 200 rpm. (2-in. throw). The samples were withdrawn aseptically every 24 hr. for the measurement of the cholesterol oxidase activity.

B. Large-scale

The 150-liter fermenter used for the large-scale fermentation contained 75 liters of sterilized modified glycerol medium. After inoculation as described in (5), the medium was maintained at 30° C. and was aerated and agitated at 0.5 vvm. and 250 rpm, respectively. Every 2.5 hr., samples were withdrawn aseptically with an automatic sampler. The samples were assayed for cholesterol oxidase activity as described in (8). The cells were harvested when the level of cholesterol oxidase reached the maximum. The time required for the fermentation was between 17–25 hr.

7. Harvesting cells

A. Small-scale

The cells were harvested (i.e., separated from the fermentation broth) by 15 min. centrifugation in a refrigerated centrifuge (duPont Co., Instrument Products Div., Sorvall Operations, Newtown, Conn.) at 12,350 × g.

B. Large-scale

The fermenter was cooled with cold water when the production of the enzyme reached the maximum. The cells were separated from the broth with a continuous centrifuge having a bowl with a capacity of 8 liters (Cepa Centrifuge, West Germany). The cells were further processed for the isolation and purification of cholesterol oxidase.

8. Determination of cholesterol oxidase activity

A. Preparation of cell fractions for the assay of cholesterol oxidase

Cholesterol oxidase can be present outside the cell or extracellularly and inside the cell or intracelluarly. Further, the intracellular enzyme can be present as free or soluble enzyme and as bound or insoluble enzyme. The extracellular enzyme can be assayed in the broth after the removal of the cells by centrifugation. To measure the intracellular enzyme, the cells are disrupted by sonication.

The cell pellet obtained by centrifugation is suspended in 1 ml. of distilled water and diluted to 20 ml. with 50 mM potassium phosphate buffer (pH 7.0). It is sonicated for 5 min. in an ice-water bath, in 1-min. bursts at 30-sec. intervals. The sonicated suspensions are centrifuged at 27,000 × g for 15 min. in the cold. The activity in the supernatant is called the intracellular, soluble activity. The pellet is resuspended in 2% sodium deoxycholate and allowed to stand on ice for 10 min. It then is centrifuged at 27,000 × g for 15 min. in the cold. The cholesterol oxidase activity in the supernatant is called the intracellular, insoluble activity. The sum of the extracellular, the intracellular soluble and the intracellular insoluble activities is called the total activity. It is also possible to measure the total activity without breaking the cells. For this purpose, the whole fermentation broth containing cells is diluted to minimize the interference due to its turbidity and is used as an enzyme solution.

9. Enzyme assay

Cholesterol oxidase activity is measured by the following technique:

A. Reagents:
1. 50 mM potassium phosphate buffer, pH 7.0 (KP buffer): 30.5 ml. 0.2 M $K_2HPO_4$ + 19.5 ml. 0.2 M $KH_2PO_4$ + water to 200 ml. final volume.
2. 0.1% dianisidine solution: 10 mg. 3,3'-dimethyoxybenzidine dihydrochloride per ml. water. No pH adjustment.
3. Reagent buffer: Add 0.5 dianisidine solution and 1.4 mg. peroxidase powder (Sigma Type II, horseradish peroxidase, RZ 1.0 – 1.5 No. P8250) to 40 ml. KP buffer, mix, dilute to 50 ml. with KP buffer. The solution will turn turbid when the dianisidine is added but clears when mixed. This solution should be kept cold until ready to use. We have stored reagent buffer at 4° C. for 3 days without problems, but routinely this reagent is prepared fresh daily.
4. Cholesterol solution: To 10 ml. Triton X-100 (available from Rohm and Haas, Philadelphia, Pa.) heated on a hot plate, add 500 mg. cholesterol powder and mix with a magnetic stirrer until solution clears. Add 90 ml. water and stir. The solution will be cloudy. Now continue mixing the flask by swirling it under a stream of cold water; the solution will become clear. Turbidity was due to detergent's coming out of solution; the coolling rehydrates the detergent and fully solubilizes the steroid. This solution is stable for 1 wk. when stored at room temperature.

B. Reactions:
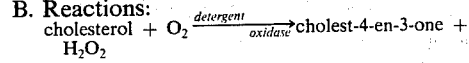
cholesterol + $O_2$ $\xrightarrow[\text{oxidase}]{\text{detergent}}$ cholest-4-en-3-one + $H_2O_2$

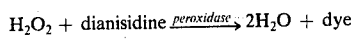
$H_2O_2$ + dianisidine $\xrightarrow{\text{peroxidase}}$ $2H_2O$ + dye C. Assay:

Six ml. of reagent buffer plus 0.1 ml. substrate plus 0.9 ml. water are combined in a test tube, mixed, and placed in a water bath set at 37° C. After 5 min., 1.0 ml. enzyme is added to give 8 ml. final volume in the tube. An initial reading at 430 nm. on a Spectronic 20 spectrophotometer (Bausch and Lomb) is recorded. The tube is replaced in the water bath. Tubes are read in the spectrophotometer every 5 min. for 25 min. Rate of color development is determined from a plot of O.D. change vs. time by averaging the O.D. change throughout the linear portion of the curve. Activity is calculated using a constant (molar extinction coefficient) previously determined for the dye system from a standard curve. Enzyme preparations are diluted so that 0.005 to 0.06 unit of cholesterol oxidase are used per assay tube.

One unit of cholesterol oxidase activity is that amount of enzyme catalyzing the production of 1 μ mole $H_2O_2$/min. at 37° C. and pH 7.0.

10. Determination of cholesterol esterase activity

The esterase activity is assayed by enzymatically measuring cholesterol released by hydrolysis of cholesterol linoleate. Cell fractions for the assay of cholesterol esterase are prepared the same as in (8)(A) above.

A. Reagents:
1. Substrate emulsion: Six-tenths gram of cholesteryl linoleate is dissolved in 10.0 g. of hot Triton X-100 and made up to 100 ml. with deionized water. The solution is cooled under running cold water to dissolve the detergent. This results in milky white emulsion of cholesteryl linoleate.
2. Esterase assay mixture: The esterase assay mixture contains 6.7 ml. of buffer solution, 0.3 ml. of cholesteryl linoleate emulsion, 0.5 ml. of cholesterol oxidase solution (1 U/ml.) and 0.5 ml. of appropriately diluted cell suspension.

B. Procedure:

Tubes containing the assay mixture without the cell suspension are shaken in a water bath at 37° C. for 15 min. Then the cell suspension is added and transmittance at 430 nm. is measured at 5-min. intervals. The amount of the enzyme is computed from the rate of color development. This assay procedure is similar to that used to measure cholesterol oxidase.

One unit of cholesterol esterase activity is that amount catalyzing the hydrolysis of 1 μ mole cholesterol linoleate/min. at 37° C. and pH 7.0.

The invention can be illustrated by the following examples. Unless otherwise indicated, concentrations given in percent are weight percent. The yields from small-scale experiments conducted using flakes are generally lower than those obtained in large-scale fermenters; however, relative effects of various fermentation parameters have been found to be similar.

EXAMPLE 1:

Effect of yeast extract

Yeast extract was essential for the production of cholesterol oxidase (Table 1). The yield of the enzyme increased from 2.7 U per liter obtained in the absence of yeast extract to 140.4 U per liter obtained in the medium with 2.0 percent yeast extract. Further increase in the concentration of yeast extract repressed the synthesis of the enzyme. Yeast extract also affected the location of the enzyme. In the presence of yeast extract, at most 5 percent of the enzyme was extracellular, and the rest was intra-cellular. The maximum enzyme titre was obtained in 24 hr.

Table 1

Effect of Yeast Extract on the Production of Cholesterol Oxidase

| Concentration of Yeast Extract % | Cholesterol Oxidase U/Liter | | Enzyme Released % of Total |
|---|---|---|---|
| | Extracellular | Total | |
| 0.0 | 2.7 | 2.7 | 100 |
| 0.1 | 0.5 | 0.5 | 100 |
| 0.5 | 0.3 | 20.5 | 2 |
| 1.0 | 2.5 | 56.2 | 5 |
| 2.0 | 2.7 | 140.5 | 2 |
| 3.0 | 0.2 | 68.1 | 0 |

Glycerol medium used in this experiment contained 0.01 percent tryptone, 0.5 percent surfactant S-3 and was supplemented with Bacto yeast extract as shown.

Surfactant S-3 is commercially available as Tween 40 from Atlas Chemicals, Wilmington, Del.

EXAMPLE 2

Effect of cholesterol (small-scale in Erlenmeyer flasks)

There was no enzyme synthesis in the absence of cholesterol (Table 2). In the medium containing 0.5 percent S-3, there was a dramatic increase in the amount of the enzyme produced on supplementing the medium with cholesterol (Table 2). The production of cholesterol oxidase reached a maximum in the medium containing 0.1 percent cholesterol. There was no further increase in the enzyme yield on increasing the concentration of cholesterol.

Cholesterol had a less pronounced effect on the cell growth. There was, at most, a 14 percent increase in the dry cell weight upon the addition of cholesterol to the medium.

Essentially similar observations were made on the effect of cholesterol on the production of the enzyme in a modified glycerol medium with 0.3 percent S-3. There was some increase in the yield of cholesterol oxidase when the concentration of cholesterol was incrased above 0.1 percent in the medium containing 0.3 percent S-3.

Table 2

Effect of Cholesterol on the Production of Cholesterol Oxidase in the Presence of 0.5 Percent Surfactant S-3

| Concentration of Cholesterol % | Cholesterol Oxidase U/Liter | Dry Cell Weight g./Liter |
|---|---|---|
| 0.0 | 0.0 | 8.3 |
| 0.02 | 76.7 | 8.9 |
| 0.05 | 126.2 | 8.8 |
| 0.1 | 143.5 | 8.5 |
| 0.2 | 124.8 | 7.7 |
| 0.5 | 142.2 | 9.5 |

The medium used to obtain the results in Table 2 contained 0.5 percent S-3; otherwise, it had the same composition as modified glycerol medium. Cholesterol concentration of the medium was adjusted as described.

EXAMPLE 3:

Effect of Surfactant S-3

The production of the enzyme was strongly affected by the surfactant S-3 (Table 3). A threefold increase in the enzyme yield was obtained on supplementation of the medium with 0.2 percent surfactant (Table 3). The maximum production of the enzyme was obtained with the concentration of S-3 between 0.2 percent to 0.3 percent (Table 3). Higher concentrations of S-3 (>0.3%) inhibited the production of the enzyme. At the most, 0.6 percent of the enzyme was released from the medium.

Table 3

Effect of Surfactant S-3 on the Production of Cholesterol Oxidase

| Concentration of S-3 | Dry Cell Weight g./Liter | Cholesterol Oxidase U/Liter |
|---|---|---|
| 0.0 | 6.0 | 39.6 |
| 0.1 | 6.9 | 85.4 |
| 0.2 | 4.7 | 129.1 |
| 0.3 | 6.6 | 124.7 |
| 0.5 | 6.0 | 72.4 |

Modified glycerol medium with varying concentration of Surfactant S-3 was used to obtain the results in Table 3.

EXAMPLE 4:

Effect of glycerol

Omission of glycerol from the medium reduced the enzyme production of 28 percent (Table 4). The enzyme level was restored almost to the control level upon addition of 0.25 percent glycerol. Further increase in the glycerol concentration did not change the enzyme level significantly.

The growth of the culture also was affected by glycerol. Almost 50-percent increase in the dry cell weight was obtained in the medium with glycerol over that obtained in the medium without glycerol (Table 4).

Table 4

Requirement of Glycerol for the Production of Cholesterol Oxidase

| Concentration of Glycerol % | Dry Cell Weight g./Liter | Cholesterol Oxidase | |
|---|---|---|---|
| | | U/Liter | % of Control[a] |
| 0.0 | 5.8 | 108.9 | 72 |
| 0.25 | 8.2 | 142.3 | 99 |
| 0.5 | 8.3 | 150.5 | 100 |

[a]Modified glycerol medium which contained 0.5% glycerol was considered the control.

EXAMPLE 5:

Sterols and cholesterol esters as inducers for cholesterol oxidase

Example 2 demonstrates the effect of cholesterol on the synthesis of cholesterol oxidase. Four sterols other than cholesterol and twelve cholesterol esters were tested for their ability to induce cholesterol oxidase. All the inducers were studied at a concentration of 0.1 percent. The most efficient inducer of cholesterol oxidase was β-sitosterol (Table 5). The total enzyme activity induced was 122 percent of that induced by cholesterol. Two other steroids, 5-α-cholestan-3-β-ol and cholest-4-en-3-one, were moderately effective in inducing the enzyme. Of the cholesterol esters tested (Table 6), cholesteryl oleate and cholsteryl linoleate induced approximately 90 percent of the enzyme induced by cholesterol while cholesteryl propionate and cholesteryl linolenate induced 75 percent and 65 percent, respectively.

Table 5
Effectiveness of Sterols as Inducers

| Sterol[b] | Total Activity (U/Liter) | Enzyme Activity % of Control[a] |
|---|---|---|
| cholesterol | 163.6 | 100 |
| β-sitosterol | 199.5 | 122 |
| 5-α-cholestan-3-β-ol | 105.6 | 65 |
| cholest-4-en-3-one | 101.0 | 62 |
| 7-dehydrocholesterol | 0 | 0 |

Modified glycerol medium was used in this experiment.
[a]The control medium contained cholesterol as the inducer.
[b]Concentration of sterol tested was 0.1 percent.

Table 6
Effectiveness of Cholesterol Esters as Inducers

| Cholesterol Ester[b] | Concentration (mmoles) | Oxidase Activity % of Control[a] |
|---|---|---|
| cholesterol | 2.6 | 100 |
| cholesteryl formate | 2.4 | 64 |
| cholesteryl propionate | 2.3 | 75 |
| cholesteryl butyrate | 2.2 | 54 |
| cholesteryl hexanoate | 2.1 | 52 |
| cholesteryl benzoate | 2.0 | 13 |
| cholesteryl p-nitrobenzoate | 1.9 | 0 |
| cholesteryl decanoate | 1.9 | 26 |
| cholesteryl laurate | 1.8 | 36 |
| cholesteryl myristate | 1.7 | 21 |
| cholesteryl palmitate | 1.6 | 14 |
| cholesteryl oleate | 1.5 | 91 |
| cholesteryl linoleate | 1.5 | 89 |
| cholesteryl linolenate | 1.6 | 65 |

Modified glycerol medium was used in this experiment.
[a]The control medium contained cholesterol as the inducer.
[b]Concentration of cholesterol esters tested was 0.1 percent.

EXAMPLE 6:

Substitutes for Bacto yeast extract

Example 1 illustrates the importance of yeast extract to the present invention. In this example several yeast hydrolysates were studied (Table 7). The effectness of 2.0 percent Amber BYF 100 and 2.0 percent Amber BYF 50X were comparable with 2.0 percent Bacto yeast extract. The best yeast hydrolysate, Amberex 1003, at a concentration of 1.0 percent stimulated enzyme production to a level 112 percent of the control. Further studies to determine the optimum concentration of Amberex 1003 demonstrated maximum activity, well over twice that of the control. Amber and Amberex yeast hydrolysates are available commercially from Amber Laboratories, Juneau, Wisconsin.

Table 7
Effectiveness of Yeast Hydrolysates for the Production of Cholesterol Oxidase

| Yeast Hydrolysates | Concentration % | Cholesterol Oxidase (U/Liter) | Enzyme Activity % of Control[a] |
|---|---|---|---|
| Difco (Bacto Yeast Extract | 2.0 | 141.2 | 100 |
| Amber BYF 100 | 0.5 | 51.7 | 37 |
|  | 1.0 | 91.8 | 65 |
|  | 2.0 | 152.4 | 108 |
|  | 5.0 | 44.2 | 34 |
| Amber BYF 50X | 0.5 | 0 | 0 |
|  | 1.0 | 0 | 0 |
|  | 2.0 | 127.3 | 90 |
|  | 5.0 | 0 | 0 |
| Amber BYF 300 | 0.5 | 53.6 | 38 |
|  | 1.0 | 65.7 | 47 |
|  | 2.0 | 95.0 | 67 |
| Amberex 1003 | 0.5 | 122.4 | 87 |
|  | 1.0 | 157.8 | 112 |
|  | 2.0 | 153.9 | 109 |
|  | 5.0 | 57.0 | 40 |

Modified glycerol medium was used in this experiment.
[a]The control medium contained Difco Yeast Extract.

Yeast extract obtained from sources other than Difco does not always work as well. In fact, considerable batch-to-batch variation from alternate sources has been found, although no such difficulty has been experienced with Difco yeast extract. Each supply of yeast extract should be tested using 2 percent Difco yeast extract as a control as in Table 7. Any yeast extract which yields 70 percent of the control when using a concentration of up to 5.0 percent in the modified glycerol medium is considered to be equivalent to Difco yeast extract for the purposes described herein.

EXAMPLE 7:

Effect of cholesterol on production of cholesterol oxidase in large-scale fermenter The 150-liter fermenter used for the large-scale fermentation was charged with 75 liters of modified glycerol medium containing 0.3 g./liter of Polyglycol P-2000 and various concentrations of cholesterol as shown in Table 8 below. After sterilization, the medium was inoculated as described hereinabove with inoculum prepared as described above. The medium was aerated at 0.6 vvm. and agitated with flat 3-bladed turbine impellers at 250 rpm. Samples were withdrawn and assayed every 2.5 hr. until the production of cholsterol oxidase reached the optimum value.

Table 8
Effect of Cholesterol on the Production of Cholesterol Oxidase in the Large-Scale Fermenter

| Concentration of Cholesterol g./Liter | Cholesterol Oxidase U/Liter |
|---|---|
| 1.0 | 177 |
| 2.0 | 356 |
| 3.0 | 749 |
| 4.0 | 888 |

Each value in Table 8 above is an average of four or more experiments.

EXAMPLE 8

Esterase and oxidase production in modified glycerol medium a. To test their effect, the sterols were added in place of cholesterol at the concentration of 0.1%. Cholesterol concentration in modified glycerol medium was 0.1%.

The highest level of the enzyme was induced by β-sitosterol and 5α-cholestan-3-β-ol (Table 9). Intermediate enzyme yields were obtained with cholesterol and cholest-4-en-3 -one. No enzyme was found in the medium with 7-dehydrocholesterol.

Table 9
Effect of Sterols on the Production of Cholesterol Esterase and Cholesterol Oxidase in Modified Glycerol Medium

| Sterols | Dry Cell Weight g./Liter | Esterase U/Liter | Oxidase U/Liter |
|---|---|---|---|
| cholesterol | 6.3 | 37.9 | 121.6 |
| β-sitosterol | 7.7 | 48.5 | 119.9 |
| 5-α-cholestan-3-β-ol | 6.8 | 49.2 | 72.3 |
| cholest-4-en-3-one | 7.9 | 21.5 | 44.0 |
| 7-dehydrocholesterol | 7.6 | 0.0 | 0.0 | b. To test the effect of various esters, 0.1% of the ester to be treated was added in place of cholesterol. Modified glycerol medium contained 0.1% cholesterol.

All six of the cholesterol esters tested in modified glycerol medium induced the esterase (Table 10). The maximum yield of the enzyme was obtained in the presence of cholesteryl linoleate. The levels of the esterase induced by the remaining five esters were about half that produced with the linoleate ester.

Table 10
Effect of Cholesterol Esters on the Production of Cholesterol Esterase and Cholesterol Oxidase in Modified Glycerol Medium

| Cholesterol Esters | Dry Cell Weight g./Liter | Esterase U/Liter | Oxidase U/Liter |
| --- | --- | --- | --- |
| cholesterol | 6.3 | 37.9 | 121.6 |
| cholesteryl propionate | 7.6 | 14.9 | 45.3 |
| cholesteryl butyrate | 7.6 | 19.6 | 38.6 |
| cholesteryl hexanoate | 8.2 | 14.9 | 59.5 |
| cholesteryl oleate | 8.2 | 16.0 | 87.2 |
| cholesteryl linoleate | 6.8 | 49.7 | 95.9 |
| cholesteryl linolenate | 7.6 | 23.0 | 71.6 |

Cholesterol oxidase production in the presence of cholesterol and $\beta$-sitosterol was significantly higher (40-60%) than the other three sterols tested (Table 9). Cholesteryl oleate and cholesteryl linoleate also induced high levels of the oxidase (Table 10). Moderate levels of the enzyme were produced in the medium with the other four cholesterol esters (Table 10).

Although the invention has been described in considerable detail with particular reference to certain preferred embodiments thereof, variations and modifications can be effected within the spirit and scope of the invention.

What is claimed is:

1. A method for the production of cholesterol esterase which comprises:
   growing a bacterium selected from *Nocardia cholesterolicum* species NRRL 5767 and NRRL 5768 in a medium comprising a cholesterol esterase inducer and at least 10 g./liter of yeast extract and
   separating the cholesterol esterase from the bacterium.

2. The method of claim 1 wherein said inducer is selected from the group consisting of cholesterol, $\beta$-sitosterol, 5-$\alpha$-cholestan-3-$\beta$-ol, cholest-4-en-3-one, cholesteryl butyrate, cholesteryl linoleate and cholesteryl linolenate, and is present in a concentration of from about 1.0 to about 10 g./liter.

3. The method of claim 2 wherein said inducer is selected from the group consisting of cholesterol, $\beta$-sitosterol, 5-$\alpha$-cholestan-3-$\beta$-ol and cholesteryl linoleate and said yeast extract is present in a concentration of from about 10 to about 30 g./liter.

4. A method for the production of cholesterol esterase which comprises:
   growing a bacterium selected from *Nocardia cholesterolicum* species NRRL 5767 and NRRL 5768 in a medium comprising from about 2.0 to about 5.0 g./liter of a cholesterol esterase conductor selected from the group consisting of cholesterol, $\beta$-sitosterol, 5-$\alpha$-cholestan-3-$\beta$-ol and cholesteryl linoleate, and from 10 to about 30 g./liter of yeast extract; and
   separating the cholesterol esterase from the bacterium.

* * * * *

UNITED STATES PATENT AND TRADEMARK OFFICE
CERTIFICATE OF CORRECTION

PATENT NO. : 4,052,263
DATED : October 4, 1977
INVENTOR(S) : P. S. Masurekar and C. T. Goodhue It is certified that error appears in the above-identified patent and that said Letters Patent are hereby corrected as shown below:

Column 16, line 25, delete "conductor" and insert --inducer--.

Signed and Sealed this

Fourth Day of April 1978

[SEAL]

Attest:

RUTH C. MASON
Attesting Officer

LUTRELLE F. PARKER
Acting Commissioner of Patents and Trademarks